United States Patent [19]

Kulprathipanja et al.

[11] Patent Number: 5,068,418

[45] Date of Patent: Nov. 26, 1991

[54] SEPARATION OF LACTIC ACID FROM FERMENTATION BROTH WITH AN ANIONIC POLYMERIC ABSORBENT

[75] Inventors: Santi Kulprathipanja, Inverness; Anil R. Oroskar, Downers Grove, both of Ill.

[73] Assignee: UOP, Des Plaines, Ill.

[21] Appl. No.: 349,272

[22] Filed: May 8, 1989

[51] Int. Cl.$^5$ ............................................. C07C 51/42
[52] U.S. Cl. ................................. 562/580; 562/589
[58] Field of Search .......................... 562/580, 589

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,706,812 | 12/1972 | De Rossett et al. | 269/674 SA |
| 4,323,702 | 4/1982 | Kawabata et al. | 562/485 |
| 4,358,464 | 11/1982 | Soehnlen | 426/271 |
| 4,552,905 | 11/1985 | Keil et al. | 521/149 |
| 4,642,397 | 2/1987 | Zinnen et al. | 568/934 |
| 4,720,579 | 1/1988 | Kulprathipanja | 562/580 |
| 4,771,001 | 9/1988 | Bailey et al. | 562/589 |

FOREIGN PATENT DOCUMENTS

| | | |
|---|---|---|
| 135728 | 4/1985 | European Pat. Off. . |
| 868926 | 6/1957 | United Kingdom . |

*Primary Examiner*—Bruce Gray
*Attorney, Agent, or Firm*—Thomas K. McBride; John F. Spears, Jr.; Jack H. Hall

[57] ABSTRACT

Lactic acid is separated from a fermentation broth by using an adsorbent comprising a water-insoluble macroreticular or gel weakly basic anionic exchange resin possessing tertiary amine or pyridine functional groups or a strongly basic anionic exchange resin possessing quaternary amine fuctional groups. The resins are in sulfate form and have a cross-linked acrylic or styrene resin matrix. Lactic acid is desorbed with water or dilute inorganic acid, e.g., sulfuric. The pH of the feed is maintained below the ionization constant (pKa) of lactic acid to obtain high selectivity.

13 Claims, 2 Drawing Sheets

SEPARATION OF LACTIC ACID FROM FERMENTATION BROTH WITH AN ANIONIC POLYMERIC ABSORBENT

FIELD OF THE INVENTION

The field of art to which this invention pertains is the solid bed adsorptive separation of lactic acid from fermentation broths containing lactic acid which may additionally contain acetic acids, carbohydrates, amino acids, ethanol, proteins and salts. More specifically, the invention relates to a process for separating lactic acid from fermentation broths containing same which process employs a non-zeolite polymeric adsorbent, which selectively adsorbs lactic acid and comprises a weakly basic anionic exchange resin possessing tertiary amine or pyridine functional groups, or a strongly basic anionic exchange resin possessing quaternary amine functional groups and mixtures thereof.

BACKGROUND OF THE INVENTION

Lactic acid is used as a food acidulant and flavoring and in pharmaceutical, plastics, textiles and other industrial formulations. The increased use of food and pharmaceutical products formulated with lactic acid has been primarily responsible for growth of worldwide production of lactic acid to about 300 million pounds per year which is expected to continue in the future.

Lactic acid is produced by a submerged culture fermentation process which employs molasses, potatoes or starch as feed and a microorganism, e.g., Lactobacillus del brueckii, L. bulgarcius or L. leichnanii. The fermentation product will contain carbohydrates, amino acids, proteins and salts as well as lactic acid, which must be separated from the fermentation broth.

For the separation of lactic acid, the calcium salt is precipitated. The resulting calcium lactate is filtered to remove heavy metals and some organic impurities. The regenerated lactic acid is separated from the precipitated $CaSO_4$, e.g., by filtration, and the resulting crude lactic acid further purified by carbon treatment and sodium ferrocyanide to remove additional organic impurities and heavy metals, respectively. After filtration, the lactic acid is contacted with an ion exchange resin to remove trace ions. The purification process is complex and high purity is difficult to obtain.

European Patent No. 135,728 discloses the separation of lactic acid from a fermentation medium with an adsorbent comprising a polymer with tertiary amino groups described in U.S. Pat. No. 4,552,905. The resins are not disclosed to be in sulfate form, as applicants have herein disclosed their invention. Furthermore, the adsorbed acid is eluted with a solvent such as methanol.

U.K. Patent No. 868,926 relates to the purification and concentration of a carboxylic acid by an ion exchange mechanism using an ion exchange resin in $OH^-$ form. After recovery of the acid by exchange with sulfurous acid, the resin is regenerated with hot water to convert the resin back to $OH^-$ form.

U.S. Pat. No. 4,323,702 discloses the separation of carboxylic acids from a synthesis mixture with strong and weakly basic anionic exchange resins in $OH^-$ form, using an organic solvent, e.g. alcohol, ketone or ester as a desorbent.

The invention herein can be practiced in fixed or moving adsorbent bed systems by batch or continuous processes, but the preferred system for this separation is a continuous countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Flow rates in the various zones may be set and regulated by a programmed flow controller. Equipment utilizing these principles are familiar, in sizes ranging from pilot plant scale (deRosset U.S. Pat. No. 3,706,812) to commercial scale with flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

SUMMARY OF THE INVENTION

This invention relates to a process for adsorbing lactic acid from a fermentation broth onto a polymeric adsorbent comprising a weakly basic anionic exchange resin possessing tertiary amine or pyridine functional groups, or a strongly basic anionic exchange resin possessing quaternary amine functional groups and mixtures thereof and thereafter recovering the lactic acid by desorption thereof with a suitable desorbent under desorption conditions. One condition for the practice of the invention that is required for achieving high selectivity is to maintain the pH of the feed solution, and thereby the adsorption zone, lower than the ionization constant (pKa) of lactic acid (3.86).

In the preferred practice of the invention, lactic acid is separated from a feed mixture comprising a fermentation broth containing same in a continuous, countercurrent simulated moving bed chromatographic process, which process employs a polymeric adsorbent comprising a weakly basic anionic exchange resin possessing tertiary amine or pyridine functional groups or a strongly basic anionic exchange resin possessing quaternary amine functional groups and mixtures thereof which comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at a upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture at a pH below the ionization constant (pKa) for lactic acid into said adsorption zone at adsorption conditions to effect the selective adsorption of said lactic acid by said adsorbent in said adsorption zone and withdrawing a raffinate output stream comprising/the nonadsorbed components of said fermentation broth from said adsorption zone;

(f) passing a desorbent material into said desorption zone at desorption conditions to effect the displacement of said lactic acid from the adsorbent in said desorption zone;

(g) withdrawing an extract output stream comprising said lactic acid and desorbent material from said desorption zone;

(h) passing at least a portion of said extract output stream to a separation means and therein separating at separation conditions at least a portion of said desorbent material; and, (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams. At least a portion of the raffinate output stream may be passed to separation means, at separation conditions, thereby separating at least a portion of said desorbent material to produce a raffinate product having a reduced concentration of desorbent material. Further, a buffer zone may be maintained immediately upstream from said desorption zone, said buffer zone defined as the adsorbent located between the desorbent input stream at a downstream boundary of said buffer zone and the raffinate output stream at an upstream boundary of said buffer zone.

Other aspects of the invention encompass details of feed mixtures, adsorbents, desorbents and operating conditions which are hereinafter disclosed.

DESCRIPTION OF THE INVENTION

Figure 1:
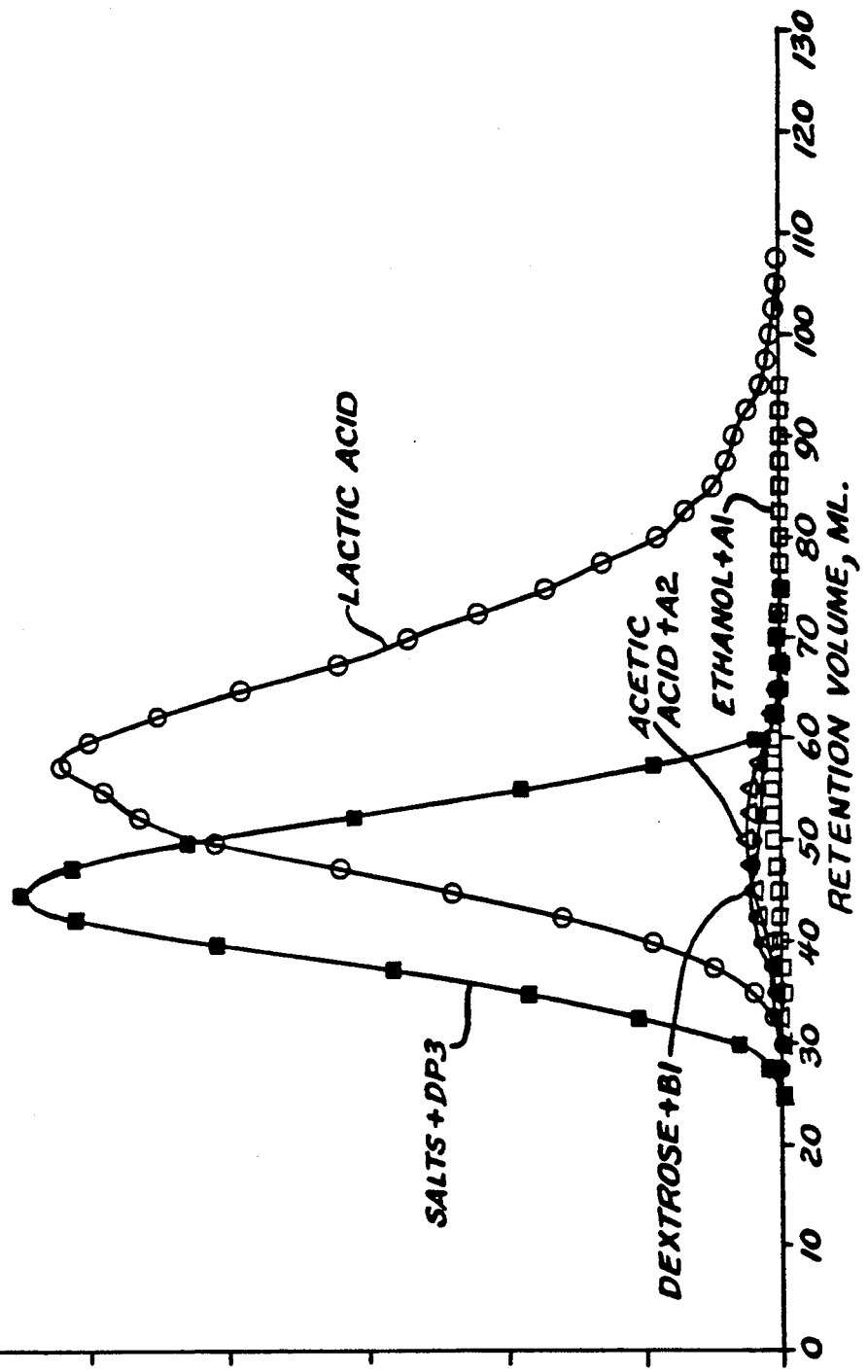
FIG. 1 is the plot of the pulse test in Example I using a weakly basic anionic exchange resin in sulfate form in a cross-linked acrylic resin matrix to separate lactic acid from a feed containing lactic acid. Lactic acid is desorbed with dilute sulfuric acid.

The feed material contemplated in this invention is the fermentation product obtained from the submerged culture fermentation of molasses, potatoes or, especially, starch by one of the microorganism, Lactobacillus del brueckii, L. bulgarcius or L. leichnanii. The fermentation product will have a composition exemplified by the following:

|  | wt. % (dry) |
|---|---|
| Lactic acid | 57.14 (9.44 wt. % wet basis) |
| Salts and DP3 | 32.90 |
| Acetic acid | 1.74 |
| Other Carbohydrates (Dextrose & Unknowns B1) | 2.58 |
| Ethanol | 0.24 |
| Unknowns (A2) | 2.73 |
| Unknowns (A1) | 1.16 |
| Unknowns not analyzed | bal. |

The salts may include K, Na, Ca, Mg and P. The unknowns will include, other than dextrose and DP3, e.g., DP2, plus other unidentified saccharides, amino acids and proteins. The composition of the feedstock may vary from that given above and still be used in the invention.

The separation of lactic acid can be enhanced significantly by adjusting the pH of the feed to a level below the ionization constant of lactic acid. The ionization constant (pKa) of lactic acid is 3.86, *Handbook of Chemistry & Physics*), 53rd Edition, 1972-3, CRC Press, and, therefore, the pH of the lactic acid feed and the adsorption zone should be below 3.86.

In aqueous solution, unionized lactic acid exists in equilibrium with lactate anions and hydrogen ions. This is shown in the following equation where the acid dissociation constant, pKa of lactic acid at 100° C. is 3.86.

Equation 1

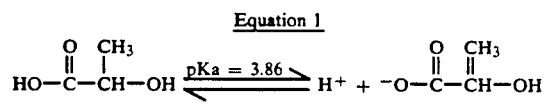

The equilibrium point of lactic acid dissociation can be shifted by varying the concentration of lactic acid, the lactate anion or the hydrogen ion.

Based on the lactic acid equilibrium and the resin properties mentioned above, nonionized lactic acid will be separated from other ionic species (including lactic anions) in the fermentation broths using the resin adsorbents described. However, the lower the pH of the solution, the greater the lactic acid recovery. Without the intention of being limited by this explanation, it appears that the nonionic lactic acid species in the solution is preferentially adsorbed on the adsorbents of the present invention either through an acid-base interaction mechanism or a hydrogen bonding mechanism or a mechanism based on a strong affinity for relatively hydrophobic species or a combination of these mechanisms.

Desorbent material used in various prior art adsorptive separation processes can vary depending upon such factors as the type of operation employed. In the swing bed system, in which the selectively adsorbed feed component is removed from the adsorbent by a purge stream, desorbent selection is not critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of the desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid phase operation of the process of the present invention, it has been found that water or dilute, inorganic acids are particularly effective desorbent materials.

Aqueous solutions of sulfuric acid, nitric acid, hydrochloric acid, phosphoric acid and mixtures thereof can be used in amounts corresponding to 0.002 to 0.2N (normal), with best results obtained with dilute sulfuric acid at 0.01 to 0.02N.

The prior art has also recognized that certain characteristics of adsorbents are highly desirable, if not absolutely necessary, to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity for one component as compared to another component. Relative selectivity can be expressed not only for one feed component as compared to another, but can also be expressed between any feed mixture component and the desorbent material. The selectivity, $\beta$, as used throughout this specification is defined as the ratio of the two components of the adsorbed phase over the ratio of the same two components in the unadsorbed phase at equilibrium conditions. Relative selectivity is shown as Equation 2 below:

Equation 2
$$\text{Selectivity} = \beta = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbents did not change composition after contacting the bed of adsorbent. In other words, there was no net transfer of material occurring between the unadsorbed and the adsorbed phases. Where selectivity of two components approaches 1.0 there is no preferential adsorption of one component by the adsorbent with respect to the other; they are both adsorbed (or nonadsorbed) to about the same degree with respect to each other. As the $\beta$ becomes less than or greater than 1.0 there is a preferential adsorption by the adsorbent for one component with respect to the other. When comparing the selectivity by the adsorbent of one component C over component D, a $\beta$ larger than 1.0 indicates preferential adsorption of component C within the adsorbent. A $\beta$ less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity, the easier the separation is to perform. Higher selectivities permit a smaller amount of adsorbent to be used. The third important characteristic is the exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Resolution is a measure of the degree of separation of a two-component system, and can assist in quantifying the effectiveness of a particular combination of adsorbent, desorbent, conditions, etc., for a particular separation. Resolution for purposes of this application is defined as the distance between the two peak centers divided by the average width of the peaks at ½ the peak height as determined by the pulse tests described hereinafter. The equation for calculating resolution is thus:

$$\text{Equation 3}$$
$$R = \frac{L_2 - L_1}{1/2(W_1 + W_2)}$$

where $L_1$ and $L_2$ are the distances, in ml, from a reference point, e.g., zero or the void volume, to the centers of the peaks of the respective components and $W_1$ and $W_2$ are the widths of the peaks at ½ the height of the peaks. The value of the resolution may have little significance where the concentration of components is low, since it is extremely difficult to determine the location of peak of the envelope and therefore, its retention volume, and also the width at one-half the peak height. In the present examples, this situation exists as to the impurity groups (A1, A2 and B2) and, therefore, although the resolution values are set forth in the examples, the values are not necessarily deemed to be of significance in assessing the separation.

The resins of the invention can be gellular (or "gel-type") or "macroreticular" as the term is used in some recent literature, namely, Kunin and Hetherington, *A Progress Report on the Removal of Colloids From Water by Macroreticular Ion Exchange Resins*, paper presented at the International Water Conference, Pittsburgh, Pa., October 1969, reprinted by Rohm & Haas Co. In recent adsorption technology, "the term microreticular refers to the gel structure per se, size of the pores which are of atomic dimensions and depend upon the swelling properties of the gel" while "macroreticular pores and true porosity refer to structures in which the pores are larger than atomic distances and are not part of the gel structure. Their size and shape are not greatly influenced by changes in the environmental conditions such as those that result in osmotic pressure variations" while the dimensions of gel structure are "markedly dependent upon the environmental conditions." In "classical adsorption", "the terms microporous and macroporous normally refer to those pores less than 20 A and greater than 200 A, respectively. Pores of diameters between 20 A and 200 A are referred to as transitional pores." The authors selected the term "macroreticular", instead, to apply to the new ion exchange resins used in this invention, which "have both a microreticular as well as a macroreticular pore structure. The former refers to the distances between the chains and crosslinks of the swollen gel structure and the latter to the pores that are not part of the actual chemical structure. The macroreticular portion of structure may actually consist of micro-, macro-, and transitional-pores depending upon the pore size distribution." (Quotes are from page 1 of the Kunin et al. article). The macroreticular structured adsorbents also have good resistance to attrition (not common to conventional macroreticular resins). In this application, therefore, all reference to "macroreticular" indicates adsorbent of the types described above having the dual porosity defined by Kunin and Hetherington. "Gel" and "gel-type" are used in their conventional sense.

One class of adsorbents to be used in the process of this invention will comprise weakly basic anion exchange resins possessing tertiary amine or pyridine functionality in sulfate form in a cross-linked polymeric matrix, e.g., acrylic or styrene. They are especially suitable when produced in bead form, have a high degree of uniform polymeric porosity, exhibit chemical and physical stability and good resistance to attrition.

Further, looking at both the tertiary amine- and pyridine-function-containing ion exchange resins of the present invention, the lone pair electron from the nitrogen atom can hydrogen bond to the lactic acid through the sulfate ion, as, for example, with a tertiary amine function-containing resin:

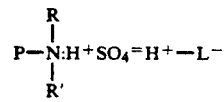

and with a pyridine function-containing resin:

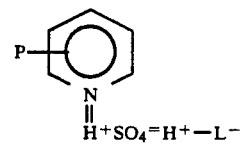

where
  P = resinous moiety
  R,R' = lower alkyl, $C_{1-3}$
  L = Lactate ion

In a feed with the pH higher than 3.86 (pKa), there will be insufficient hydrogen ions for the hydrogen bond formation with the sulfate ion; lactic acid will not be adsorbed by the resin and will "break through" with salts and carbohydrates at the beginning of the cycle.

Adsorbents such as just described are normally available as the chloride, but can be converted to the sulfate form by the process described hereinafter. "Amberlite" adsorbent resins, manufactured by the Rohm and Haas Company, are suitable and those known to be effective for use by this invention include Amberlite adsorbents XE-275 (IRA-35) and IRA-68, described in Rohm and Haas Company literature as "insoluble in all common solvents and having open structure for effective adsorption and desorption of large molecules without loss of capacity, due to organic fouling." Also suitable are AG3-X4A and AG4-X4 manufactured by Bio Rad and comparable resins sold by Dow Chemical Co., such as Dowex 66, and Dow experimental resins made in accordance with U.S. Pat. Nos. 4,031,038 and 4,098,867.

The available weakly basic polymeric adsorbents of this class will differ somewhat in physical properties such as porosity (volume percent), skeletal density and nominal mesh sizes, and perhaps more so in surface area, average pore diameter and dipole moment. The preferred adsorbents will have a surface area of 10-2000 square meters per gram and preferably from 100-1000 m²/g. Specific properties of the materials listed above can be found in company literature and technical brochures, such as those in the following Table 1 which are incorporated herein by reference. Others of the general class are also available.

TABLE 1

| Adsorbent | Weakly Basic Anionic Exchange Resins | |
|---|---|---|
| | Matrix Type | Reference to Company Literature |
| AG3-4A (Bio Rad) | Polystyrene | Chromatography Electrophoresis Immunochemistry Molecular Biology-HPLC-Price List M April 1987 (Bio-Rad) |
| AG4-X4 | Acrylic | Chromatography Electrophoresis |

TABLE 1-continued

| | Weakly Basic Anionic Exchange Resins | |
|---|---|---|
| Adsorbent | Matrix Type | Reference to Company Literature |
| Dow Experimental Resins | Polystyrene | Immunochemistry Molecular Biology-HPLC-Price List M April 1987 (Bio-Rad) U.S. Pat. Nos. 4,031,038 and 4,098,867 |
| Dowex 66 | Polystyrene | Material Safety Data Sheet Printed February 17, 1987 (Dow Chemical U.S.A.) |
| IRA-35 (XE-275) | Acrylic | Amberlite Ion Exchange Resins (XE-275) Rohm & Haas Co. 1975 |
| IRA-68 | Acrylic | Amberlite Ion Exchange Resins-Amberlite IRA-68 Rohm & Haas Co. April 1977 |

Applications for Amberlite polymeric adsorbents suggested in the Rohm and Haas Company literature include decolorizing pulp mill bleaching effluent, decolorizing dye wastes and removing pesticides from waste effluent. There is, of course, no hint in the literature of the effectiveness of Amberlite polymeric adsorbents in the separation of lactic acid from fermentation broths.

A second class of adsorbents to be used in the process of this invention will comprise strongly basic anion exchange resins processing quaternary ammonium functionality in a cross-linked polymeric matrix, e.g., divinylbenzene cross-linked acrylic or styrene resins. It is also necessary that these be in the sulfate form, as described below. They have a high degree of uniform polymeric porosity and exhibit chemical and physical stability and are especially suitable when produced in bead form.

Looking at the quaternary ammonium function-containing strongly basic anionic exchange resins of the invention, the quaternary ammonium ion has a positive charge and can form an ionic bond with the sulfate ion. The sulfate form of quaternary ammonium anion exchange resin has a weakly basic property, which, in turn, can adsorb lactic acid through an acid-base interaction.

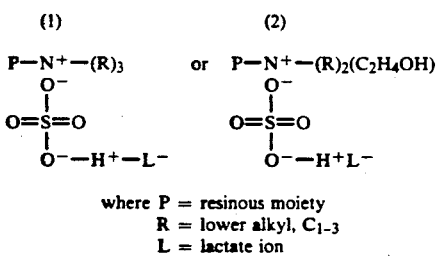

where P = resinous moiety
R = lower alkyl, $C_{1-3}$
L = lactate ion

Adsorbents such as just described are manufactured by the Rohm and Haas Company, and sold under the trade name "Amberlite". The types of Amberlite polymers known to be effective for use by this invention are referred to in Rohm and Haas Company literature as Amberlite IRA 400 and 900 series adsorbents described in the literature as "insoluble in all common solvents, open structure for effective adsorption and desorption of large molecules without loss of capacity, due to organic fouling." Also suitable are AG1, AG2 and AGMP-1 resins manufactured by Bio Rad and comparable resins sold by Dow Chemical Co., such as Dowex 1, 2, 11, MSA-1 and MSA-2, etc. Also useful in this invention are the so-called intermediate base ion exchange which are mixtures of strong and weak base exchange resins. Among these are the following commercially available resins: Bio-Rex 5 (Bio-Rad 1); Amberlite IRA-47 and Duolite A-340 (both Rohm & Haas). For example, they may be useful where a basic ion exchange resin is needed which is not as basic as the strong base resins, or one which is more basic than the weakly basic resins.

Various strongly basic anionic exchange resins are available and will also differ in physical properties such as porosity (volume percent), skeletal density, nominal mesh sizes, surface area, average pore diameter and dipole moment. The preferred adsorbents will have a surface area of 10–2000 square meters per gram and preferably from 100–1000 $m^2/g$. Specific properties of the materials listed above can be found in company literature and technical brochures, such as those mentioned in the following Table 2 which are incorporated herein by reference.

TABLE 2

| | STRONGLY BASIC ANIONIC EXCHANGE RESINS | |
|---|---|---|
| Adsorbent | Matrix Resin Type | Reference to Company Literature |
| IRA 458 (Rohm & Haas) | Acrylic gel-type | Amberlite Ion Exchange Resins 1986 & Technical Bulletin IE-207-74 84 |
| IRA 958 | Acrylic macroporous | Technical Bulletin and Material Safety Data Sheet are available |
| IRA 900 | Polystyrene macroporous | Technical Bulletin is available and Amberlite Iion Exchange Resins, IE-100-66. |
| IRA 904 | Polystyrene macroporous | Technical Bulletin, 1979 and IE-208/74, Jan. 1974 |
| IRA 910 | Polystyrene macroporous | Technical Bulletin, 1979 and IE-101-66, May 1972 |
| IRA 400, 402 | Polystyrene macroporous | Amberlite Ion Exchange Resins, Oct., Sept. 1976, April 1972 and IE-69-62, October 1976 |
| IRA 410 | Polystyrene gel-type | Amberlite Ion Exchange Resins IE-72-63, August 1970 |
| AG 1 (Bio Rad) | Polystyrene gel-type | Chromatography Electrophoresis Immunochemistry Molecular Biology HPLC, Price List M April 1987 |
| AG 2 | Polystyrene gel-type | Chromatography Electrophoresis Immunochemistry Molecular Biology HPLC, Price List M April 1987 |
| AG-MP-1 | Polystyrene macroporous | Chromatography Electrophoresis Immunochemistry Molecular Biology HPLC, Price List M April 1987 |
| Bio Rex 5 (Bio Rad) | Mixture of strong base and weak base resins (e.g. AG-2 and AG-3 or AG-4 | Chromatography Electrophoresis Immunochemistry Molecular Biology HPLC, Price List M April 1987 |

In the practice of the invention, the adsorbents set forth above are in the sulfate form. Therefore, the commercial adsorbent listed above must be converted from the form as received, in most cases the chloride, or the free base to the sulfate, which in itself is known in the art. As applicants practice the conversion, the adsorbent is placed in a column and 1N $H_2SO_4$ is passed through the column at a liquid hourly space velocity (LHSV) of 1 $hr^{-1}$ until the adsorbent has been contacted with a 100% excess of the amount of sulfate ion calculated to convert the entire resin capacity. After washing the adsorbent bed with 5 bed volumes of water, the adsorbent is ready for use.

The adsorbent may be employed in the form of a dense compact fixed bed which is alternatively contacted with the feed mixture and desorbent materials. In the simplest embodiment of the invention the adsorbent is employed in the form of a single static bed in which case the process is only semicontinuous. In another embodiment a set of two or more static beds may be employed in fixed bed contacting with appropriate valving so that the feed mixture is passed through one or more of the other beds in the set. The flow of feed mixture and desorbent materials may be either up or down through the desorbent. Any of the conventional apparatus employed in static bed fluid-solid contacting may be used.

Countercurrent moving bed or simulated moving bed countercurrent flow systems, however, have a much greater separation efficiency than fixed adsorbent bed systems and are therefore preferred. In the moving bed or simulated moving bed processes the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in the above mentioned U.S. Pat. No. 2,985,589.

Although both liquid and vapor phase operations can be used in many adsorptive separation processes, liquid-phase operation is preferred for this process because of the lower temperature requirements and because of the higher yields of extract product than can be obtained with liquid-phase operation over those obtained with vapor-phase operation. Adsorption conditions will include a temperature range of from about 20° C. to about 200° C. with about 65° C. to about 100° C. being more preferred, a pressure to ensure liquid phase, e.g. in the range of from about atmospheric to about 500 psig (3450 kPa gauge) with 50 psi to 100 psi being more preferred and a pH below the ionization constant (pKa) of lactic acid. Desorption conditions will include the same range of temperatures and pressures as used for adsorption conditions.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a helical column of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent, is injected for a duration of several minutes. Desorbent flow is resumed, and the tracer and the extract component or the raffinate component (or both) are eluted as in a liquid-solid chromatographic operation. The effluent can be analyzed on stream or, alternatively, effluent samples can be collected periodically and later analyzed separately by analytical equipment and traces of the envelopes of corresponding component peaks developed.

From information derived from the test adsorbent, performance can be stated in terms of void volume, net retention volume for an extract or a raffinate component, selectivity for one component with respect to the other, the rate of desorption of an extract component by the desorbent and resolution. The net retention volume (NRV) of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during the time interval represented by the distance between the peak envelopes. Selectivity, $\beta$, for an extract component with respect to a raffinate component may be characterized by the ratio of the distance between the center of the extract component peak envelope and the tracer peak envelope (net retention volume or NRV) (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent pumped during this time interval. Resolution is defined earlier.

The following examples are presented to illustrate the relationships that make the process of my invention possible. The examples are not intended to unduly restrict the scope of claims attached hereto.

EXAMPLE I

In this example a pulse test was run with a weakly basic anionic exchange resin having tertiary amine functionality in sulfate form in a divinylbenzene crosslinked acrylic resin matrix to determine the ability of the adsorbent to separate lactic acid from its fermentation mixture of carbohydrates (DP1, DP2, DP3, including dextrose), ions of salts, including $Na^+$, $K^+$, $Mg^{++}$, $Ca^{++}$, $Cl^-$, $SO_4^=$, $PO_4^\equiv$ and $NO_3^-$, amino acids and proteins. The test was run at 60° C. The pH of the feed was 2.0. Lactic acid was desorbed with 0.02N sulfuric acid. The fermentation feed mixture had the following composition:

| Feed Composition | Wt. % (Dry Basis) |
| --- | --- |
| Lactic Acid | 57.14 |
| DP3 and Salts ($K^+$, $Na^+$, $Ca^{++}$, $Mg^{++}$ $P^{+++}$) | 32.90 |
| Dextrose, DP2 and Unknowns (B1) | 2.58 |
| Acetic Acid | 1.74 |
| Ethanol | 0.24 |
| Unknowns (A2) | 2.73 |
| Unknowns (A1) | 1.16 |

The adsorbent was Amberlite IRA-35 (Rohm and Haas Company) which was treated with 1N sulfuric acid at an LHSV of 1 hr$^{-1}$ as aforesaid to convert the entire resin capacity to sulfate. In the treatment, 70 ml of adsorbent was placed in a column, and 350 ml of 1N H$_2$SO$_4$ was passed through the column. The adsorbent was then washed with 350 ml of deionized water (5 bed volume) before use.

Retention volumes and resolution were obtained using the pulse test apparatus and procedure previously described. Specifically, the adsorbent was tested in a 70 cc straight column using the following sequence of operations for the pulse test. Desorbent material was continuously run upwardly through the column containing the adsorbent at a flow rate of 1.25 cc/min. (a nominal liquid hourly space velocity (LHSV) of about 1.0 hr$^{-1}$). At a convenient time the flow of desorbent material was stopped, and a 5 cc sample of feed mixture was injected into the column via a sample loop and the flow of desorbent material was resumed. Samples of the effluent were automatically collected in an automatic sample collector and later analyzed for salts and lactic acid by chromatographic analysis. Carbohydrates were not separately analyzed in these examples nor were other minor ingredients, amino acids and proteins. Acetic acid was analyzed with unknowns A2 (probably one of the groups of carbohydrates); dextrose was analyzed with unknowns A1. A third group of unknown components, B1, probably also carbohydrates, was also analyzed with ethanol. From the analysis of these samples, peak envelope concentrations were developed for the feed mixture components. The net retention volume (NRV) for the lactic acid is the distance from the midpoint of the salt envelope (as the reference point) to the midpoint of the lactic acid envelope. NRV is calculated as the difference between gross retention volume (GRV) of the component and the void volume (GRV of the tracer or raffinate component, in this case, the salts and DP3). Selectivity, $\beta$, was calculated as previously indicated, as the ratio of the net retention volume (NRV) of the extract product to the NRV of the component. The resolution, R, is calculated from Equation 3, given earlier.

The results for the pulse test are shown in the following Table 3.

TABLE 3

| Component | NRV (ml) | GRV (ml) | $\beta$ | Width at Half Height (ml) | R |
|---|---|---|---|---|---|
| Salts & DP3 | 0.0 | 45.3 | 0.00 | 15.9 | 0.63 |
| Lactic Acid | 12.8 | 58.1 | ref. | 24.9 | — |
| B1 + Dextrose | 2.9 | 48.2 | 4.41 | 20.3 | 0.44 |
| Unk. A1 + Ethanol | 11.0 | 56.3 | 1.16 | 19.8 | 0.08 |
| A2 + Acetic Acid | 5.3 | 50.6 | 2.41 | 20.4 | 0.33 |

The results are also shown in FIG. 1 in which it is clear that lactic acid is more strongly adsorbed than the other components.

EXAMPLE II

This example presents the results of using a strongly basic anionic resin having quaternary ammonium functionality in sulfate form in a divinylbenzene crosslinked acrylic resin matrix (Amberlite IRA958) to separate the same feed mixture as Example I at two different pHs, i.e., below the pKa=3.86 of lactic acid and two concentrations. The same procedure and apparatus previously described in Example I were used in both the separation and the preparation of the sulfate form of the resin.

Figure 2:
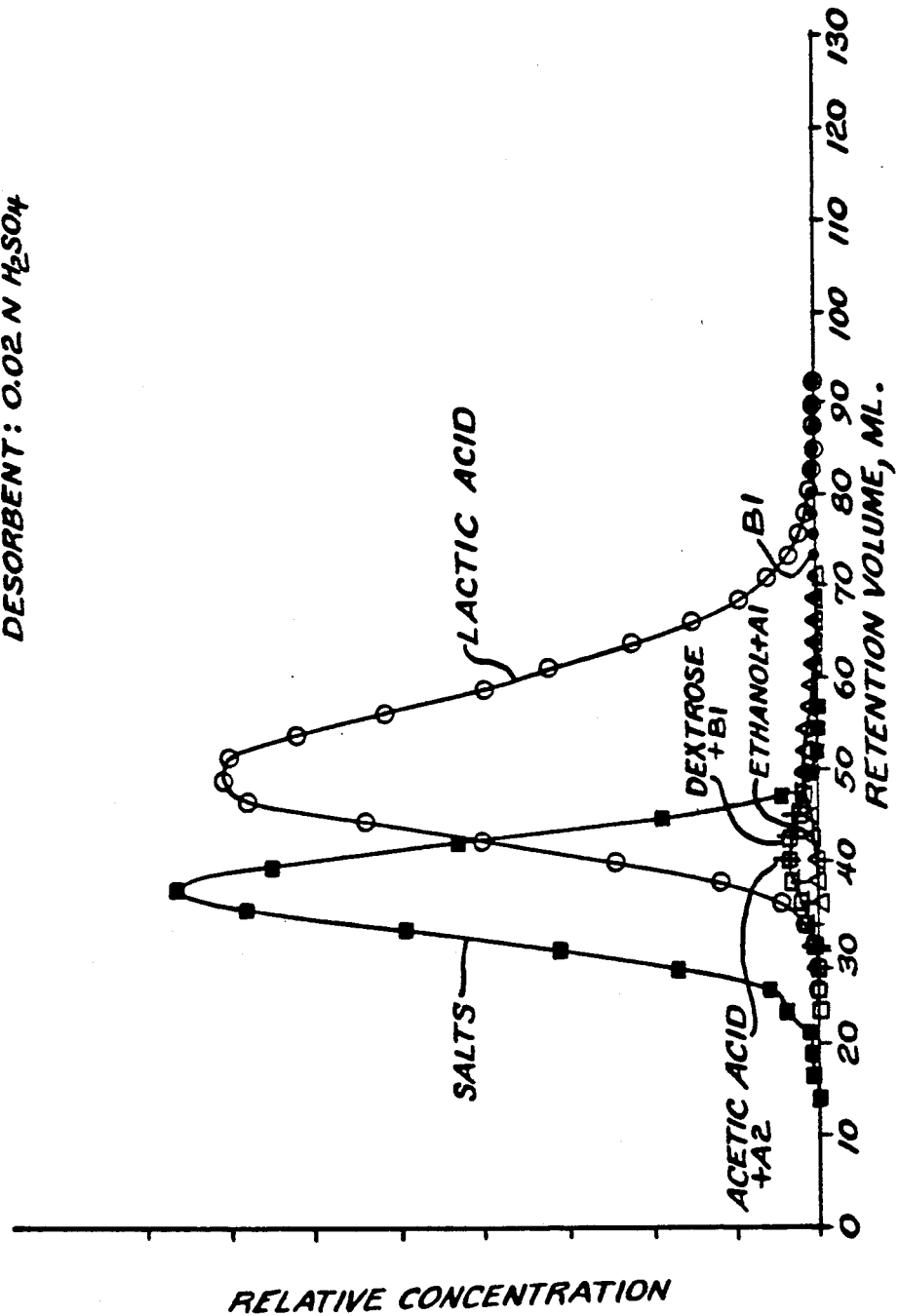
FIG. 2 is the plot of the pulse test of Example II with a strongly basic anionic exchange resin adsorbent in sulfate form in a cross-linked acrylic resin matrix. The lactic acid is desorbed with dilute sulfuric acid.

FIG. 2 is a graphical presentation of the result of the first pulse test using Amberlite IRA958 at a pH of 2.0 and lactic acid concentration of 9.44% (wet), using 0.02N H$_2$SO$_4$ as the desorbent. In the second run, the feed was diluted with water to 30% lactic acid and pH was 1.5. The results of Test No. 1 and 2 are shown in the following Tables 4 and 5, respectively:

TABLE 4

| Component | NRV (ml) | GRV (ml) | $\beta$ | Width at Half Height (ml) | R |
|---|---|---|---|---|---|
| Salts & DP3 | 0.0 | 37.3 | 0.00 | 11.0 | 0.93 |
| Lactic Acid | 13.8 | 51.0 | ref. | 18.5 | — |
| Unk. B1 | 38.2 | 75.5 | 0.36 | 18.9 | 1.31 |
| Unk. B2 + Dextrose | 3.3 | 40.6 | 4.12 | 14.1 | 0.63 |
| Unk. A1 + Ethanol | 12.7 | 50.0 | 1.09 | 14.6 | 0.06 |
| Unk. A2 + Acetic Acid | 5.0 | 42.2 | 2.77 | 12.6 | 0.57 |

TABLE 5

| Component | NRV (ml) | GRV (ml) | $\beta$ | Width at Half Height (ml) | R |
|---|---|---|---|---|---|
| Salts & DP3 | 0.0 | 39.9 | 0.00 | 12.6 | 0.86 |
| Lactic Acid | 13.2 | 53.1 | ref. | 18.4 | — |
| B2 + Dextrose | 2.8 | 42.7 | 4.74 | 15.5 | 0.62 |
| A1 + Ethanol | 4.5 | 44.4 | 2.95 | 11.6 | 0.59 |
| A2 + Acetic Acid | 10.6 | 50.5 | 1.25 | 14.6 | 0.17 |

Using the same adsorbent as above, an additional separation of the same 30% lactic acid feed as above was made, at a pH of 1.5 and desorbent concentration of 0.002N H$_2$SO$_4$. The results are shown in the following Table 6.

TABLE 6

| Component | NRV (ml) | GRV (ml) | $\beta$ | Width at Half Height (ml) | R |
|---|---|---|---|---|---|
| Salts & DP3 | 0.0 | 38.2 | 0.00 | 12.2 | 1.0 |
| Lactic Acid | 16.8 | 55.0 | ref. | 21.4 | — |
| B2 + Dextrose | 5.7 | 43.9 | 2.94 | 21.7 | 0.51 |
| Unk. A1 + Ethanol | 4.4 | 42.6 | 3.81 | 13.9 | 0.70 |
| A2(2) + Acetic Acid | 12.2 | 50.4 | 1.37 | 3.8 | 0.36 |

An excellent separation was achieved in each case.

EXAMPLE III

In this example, the same adsorbent was used as in Example III. The feed was a synthetic lactic acid broth containing 20% (wt.) lactic acid and a deacidified fermentation broth with the following composition:

| Feed Components | wt. % |
|---|---|
| Lactic Acid | 20% |
| Salts | 10% |
| Carbohydrates, Amino Acids and Proteins | 5% |
| Other Impurities and Water | balance |

The desorbent was water. The pH of the feed was 2.5. The results are shown in the following Table 7.

TABLE 7

| Component | NRV (ml) | GRV (ml) | β | Width at Half Height (ml) | R |
| --- | --- | --- | --- | --- | --- |
| Salts | 0.0 | 37.9 | 0.00 | 10.0 | 1.97 |
| Carbohydrates + Unknown Amino Acids and Proteins | 7.1 | 43.0 | 3.79 | 17.3 | 0.98 |
| Lactic Acid | 26.8 | 64.8 | 1.00 | 23.3 | — |

What is claimed is:

1. A process for separating lactic acid from a fermentation broth mixture containing lactic acid produced by a fermentation process comprising contacting said feed mixture with an anionic polymeric adsorbent comprising a weakly basic anionic exchange resin possessing pyridine functional groups at adsorption conditions selected to selectively adsorb said lactic acid and thereafter recovering said lactic acid from said adsorbent with a desorbent consisting essentially of water or a dilute inorganic acid at desorption conditions, said adsorption conditions including a pH below the ionization constant (pKa) of lactic acid.

2. The process of claim 1 further characterized in that said adsorption and desorption conditions include a temperature within the range of from about 20° C. to about 200° C. and a pressure within the range of from about atmospheric to about 500 psig (3450 kPa gauge).

3. The process of claim 1 further characterized in that said desorbent is 0.002 to 0.2N $H_2SO_4$.

4. The process of claim 1 further characterized in that the pH of said feed mixture is lower than the ionization content (pKa) of lactic acid.

5. The process of claim 1 further characterized in that said adsorbent comprises a pyridine functional group supported on a matrix selected from the group consisting of crosslinked polystyrene resins and crosslinked acrylic resins.

6. The process of claim 1 wherein said adsorbent is in the sulfate form.

7. A process for separating lactic acid from a fermentation broth mixture containing lactic acid produced by a fermentation process comprising contacting said feed mixture with an anionic polymeric adsorbent selected from the group consisting of a weakly basic anionic exchange resin processing tertiary amine functional groups and a strongly basic anionic exchange resin possessing quaternary amine functional groups and mixtures thereof at adsorption conditions selected to selectively adsorb said lactic acid and thereafter recovering said lactic acid from said adsorbent with a desorbent comprising water or a dilute inorganic acid at desorption conditions, said adsorption conditions including a pH below the ionization constant (pKa) of lactic acid.

8. The process of claim 7 wherein the pH of said feed mixture is lower than the ionization constant (pKa) of lactic acid.

9. The process of claim 7 wherein said adsorbent is in the sulfate form.

10. The process of claim 7 wherein said adsorbent comprises a tertiary amine functional group supported on a matrix comprising a crosslinked acrylic resin.

11. The process of claim 7 wherein said adsorbent comprises a quaternary ammonium functional group supported on a matrix comprising a crosslinked acrylic resin.

12. The process of claim 7 wherein said adsorption and desorption conditions include a temperature within the range of from about 20° C. to about 200° C. and a pressure within the range of from about atmospheric to about 500 psig (3450 kPa gauge).

13. The process of claim 7 wherein said desorbent is 0.002 to 0.2N $H_2SO_4$.

* * * * *